US006764709B2

(12) United States Patent
Flanagan

(10) Patent No.: US 6,764,709 B2
(45) Date of Patent: Jul. 20, 2004

(54) METHOD FOR MAKING AND MEASURING A COATING ON THE SURFACE OF A MEDICAL DEVICE USING AN ULTRAVIOLET LASER

(75) Inventor: Aiden Flanagan, Co. Galway (IE)

(73) Assignee: SciMed Life Systems, Inc., Maple Grove, MN (US)

( * ) Notice: Subject to any disclaimer, the term of this patent is extended or adjusted under 35 U.S.C. 154(b) by 171 days.

(21) Appl. No.: 10/007,457

(22) Filed: Nov. 8, 2001

(65) Prior Publication Data

US 2003/0087024 A1 May 8, 2003

(51) Int. Cl.[7] .............................. B05D 7/14; B05D 7/20; B05D 3/12; A61L 27/00

(52) U.S. Cl. ....................... 427/2.1; 427/2.24; 427/2.25; 427/2.3; 427/553; 427/554; 427/555; 427/558; 427/331

(58) Field of Search ................................. 427/2.1, 2.24, 427/2.25, 2.3, 553, 554, 555, 558, 331

(56) References Cited

U.S. PATENT DOCUMENTS 4,957,770 A * 9/1990 Howarth ........................ 427/9
5,418,349 A * 5/1995 Swain et al. ........... 219/121.84
5,584,875 A * 12/1996 Duhamel et al. ............. 600/36
5,780,807 A * 7/1998 Saunders ............... 219/121.71
5,925,069 A * 7/1999 Graves et al. ................ 607/36
6,066,168 A * 5/2000 Lau et al. .................. 623/1.16
6,153,252 A * 11/2000 Hossainy et al. ............ 427/2.3
6,503,556 B2 * 1/2003 Harish et al. .............. 427/2.24
6,558,733 B1 * 5/2003 Hossainy et al. .......... 427/2.24

OTHER PUBLICATIONS

C. Momma et al., Laser Cutting of Alotted Tube Coronary Stents–State–of–the–Art and Future Developments, Progr. Biomed. Res. 39 (Feb. 1999) pp. 39–44.*
Perry et al., *Ultrashort–Pulse Laser Maching,* Section K–ICALEO 1998, 1–20.
Momma et al., *Progress in Biomedical Research* 39 (Feb. 1999) 39–44.
Website of Zygo Co., http://www.zygo.com/zygohome.htm and http://zygo.com/nv5000/nv5000.htm.
Website of VEECO Instruments, http://www.veeco.com/html/sub__products__productdisplay.asp__Q__GroupID__E__13.
Website of Lambda Physik, http://www.lambdaphysik.com.

* cited by examiner

*Primary Examiner*—Shrive P. Beck
*Assistant Examiner*—Jennifer Kolb Michener
(74) *Attorney, Agent, or Firm*—Jones Day

(57) ABSTRACT

This invention relates to a method for manufacturing an implantable medical device, having a surface covered with a coating that can include a desired amount of a biologically active material, using an ultraviolet (UV) laser. The invention also pertains to a method for manufacturing an implantable medical device having a surface covered with a coating having more than one layer wherein a desired portion of the top layer is ablated with an ultraviolet (UV) laser. Also, the invention relates to a method for measuring a thickness of a coating applied to an implantable medical device. Furthermore, the invention is directed to a method for manufacturing an implantable medical device having a surface covered with a coating free of webbing or cracking.

10 Claims, 5 Drawing Sheets

METHOD FOR MAKING AND MEASURING A COATING ON THE SURFACE OF A MEDICAL DEVICE USING AN ULTRAVIOLET LASER

FIELD OF THE INVENTION

This invention relates generally to a method for manufacturing an implantable medical device. More specifically, the invention relates to a method for manufacturing an implantable medical device having a coated surface. More particularly, the invention is directed to a method for manufacturing an implantable medical device, having a surface covered with a coating that can include a desired amount of a biologically active material, using an ultraviolet (UV) laser. The invention also pertains to a method for manufacturing an implantable medical device having a surface covered with a coating having more than one layer wherein a desired portion of the top or outer layer is ablated with an ultraviolet (UV) laser. Also, the invention relates to a method for measuring a thickness of a coating applied to an implantable medical device. Furthermore, the invention is directed to a method for manufacturing an implantable medical device having a surface covered with a coating free of webbing or cracking.

BACKGROUND OF THE INVENTION

There are various kinds of medical devices that can be implanted in a human body. For example, medical devices, such as stents, are implanted into a body lumen, such as a blood vessel, where it stays permanently, to keep the vessel open and to improve blood flow to the heart muscle and relieve symptoms and used to reduce restenosis after balloon angioplasty or other procedures involving catheters. Usually, the suitable stents include a stent having a cylindrical shape. The walls of the cylindrical structure can be formed of metal or polymer with openings therein, e.g., a mesh. The medical devices can also be positioned in other parts of the body, such as the kidneys or the brain. The procedure for implanting the medical device is fairly common, and various types of medical devices or stents have been developed and actually used.

To make the medical device surface more biocompatible, they have been coated with polymers. Further, there are various types of polymer coatings for medical devices that may contain a biologically active material, such as a drug, that are delivered to an afflicted area of a body. Drugs may be either bonded chemically, physically or absorbed in the polymer matrix of the coating. Also, for the purpose of obtaining drug delivery medical devices or stents, the drugs may be directly coated or immobilized onto the devices, e.g. using a binding molecule between the drug molecule and the device surface. For example, U.S. Pat. No. 6,099,562 to Ding et al. discloses a stent having an undercoat containing a biologically active material covered by a topcoat substantially free of pores, and U.S. Pat. No. 5,879,697 to Ding et al. discloses a coated stent wherein the coating contains a reservoir layer containing a biologically active material. Pinchuk, in U.S. Pat. No. 5,092,877, discloses a stent of a polymeric material that may have a coating associated with the delivery of drugs. A patent to Sahatjian, U.S. Pat. No. 5,304,121, discloses a coating applied to a stent consisting of a hydrogel polymer and a pre-selected drug such as cell growth inhibitors or heparin. Thus, a number of various coatings for medical devices have been used. Such coatings have been applied to the surface of a medical device mostly by either spray-coating or dip-coating the device with a coating solution.

When a drug whose dosage must be strictly controlled is contained in the coating of the medical device, the amount of coating present on the medical device must be accurately adjusted. Previously, the only way to adjust the amount of coating on a medical device is to control the process parameters used to spray-coat the coating composition on the surface of the medical device to form the coating, such as controlling the spraying time and the flow rate of the coating solution. However, such control does not permit sufficiently accurate placement of the desired amount of coating material or drug contained in the coating material to be placed on the medical device. Also, when a dip coating method is used to form the coating, the amount of coating placed on the surface of the medical device cannot be controlled precisely. In addition, no matter what method is used for forming the coating, there has been no way to efficiently remove or trim excess or undesired coating from the coated medical device. Therefore, a method to manufacture a medical device having a desired amount of coating is needed.

Also, due to complex geometry of certain medical devices such as a stent, a webbing of coating material can form in the openings of these medical devices. More specifically, for instance, when a stent having openings in its sidewall is coated with a coating material, webbings, bindings or bridges of the coating material can form in the openings, at small gaps or corners between stent struts. This is especially true, when the stent has struts that are very close to each other or has struts that have bends in them. However, there has been no efficient way to remove or trim such webbings, bindings or bridges of coating material. Hence, an object of the invention is to provide a method to remove or trim this webbing, binding or bridging from a coated medical device.

In addition, it is not always desirable to have an even or uniform coating on an entire coated surface of a medical device. For example, depending on its geometry, a stent may have a portion where a thick coating may easily crack and cause problems. More specifically, when a self-expandable stent is placed into its restrained state, its struts lie in close proximity to each other. The coating on some struts may adhere to coating on other struts. When the stent is expanded, the adhered coating may be torn off. Likewise when a balloon-expandable stent is collapsed for implantation, the coating on certain struts may adhere to the coating on other struts because the struts are placed in close proximity to each other. Such adhered coating may be cracked or removed from the struts when the stent is expanded. If a portion of the coating can be removed from the struts so that the coating on the struts are made thinner and less likely to adhere to each other, the cracking of the coating may be reduced. However, previously, there has been no way to efficiently make a portion of a coating on a stent thinner. Thus, a further object of the invention is to provide a method to thin a portion of the coating on a medical device.

SUMMARY OF THE INVENTION

These and other objectives are accomplished by the present invention. To achieve the aforementioned objectives, a method has been invented for manufacturing an implantable medical device having a surface adapted for exposure to body tissue of a patient, wherein at least a portion of the surface is covered with a coating having a desired amount of a biologically active material. Specifically, in the method, a coating composition containing the biologically active material is applied to a portion of the surface of the medical device in a manner such that a coating containing an amount of the biologically active material in excess of the desired amount of biologically active material is formed. Then the amount of biologically active material in the coating that is in excess of the desired amount of biologically active material is determined. A portion of the coating is ablated using an ultraviolet (UV) laser in order to remove the coating containing the excess biologically active material.

Another embodiment of the present invention is a method for manufacturing an implantable medical device having a surface adapted for exposure to body tissue of a patient, wherein at least a portion of the surface is covered with a coating having at least two layers and containing a biologically active material. In the method, a first coating composition and a second composition are applied, in turn, on at least a portion of the surface of the medical device. A portion of the second coating layer is then ablated using an ultraviolet (UV) laser.

Yet another embodiment of the invention is a method for measuring a thickness of a coating applied to at least a portion of a surface of an implantable medical device. In the method, a portion of the coating is ablated with an ultraviolet (UV) laser having pulse length shorter than about 100 nanoseconds and a repetition rate less than about 100 Hertz to expose a portion of the surface of the medical device and to create a step having a height in the coating. The thickness of the coating is determined by measuring the height of the step by using a white light interferometer.

Furthermore, another embodiment of the present invention is a medical device having a surface adapted for exposure to body tissue of a patient, wherein the surface has a plurality of openings therein and wherein at least a portion of the surface is covered with a coating in a manner such that the openings are substantially free of coating and a method for manufacturing the medical device. In the method, after applying a coating composition to the surface of the medical device to form a coating thereon, coating present in the openings of the surface is ablated using an ultraviolet (UV) laser having pulse length shorter than about 100 nanoseconds and a repetition rate less than about 100 Hertz.

Another embodiment of the present invention is a method for manufacturing an expandable stent having a surface adapted for exposure to body tissue of a patient. At least a portion of the surface of the stent is comprised of a plurality of struts, and the struts are covered with a coating substantially free of cracks. In the method, after applying a coating composition to at least one of the struts to form a coating thereon, a portion of the coating on the strut is removed using an ultraviolet (UV) laser, having pulse length shorter than about 100 nanoseconds and a repetition rate less than about 100 Hertz, to prevent the coating from cracking.

DETAILED DESCRIPTION OF THE INVENTION

Figure 1:
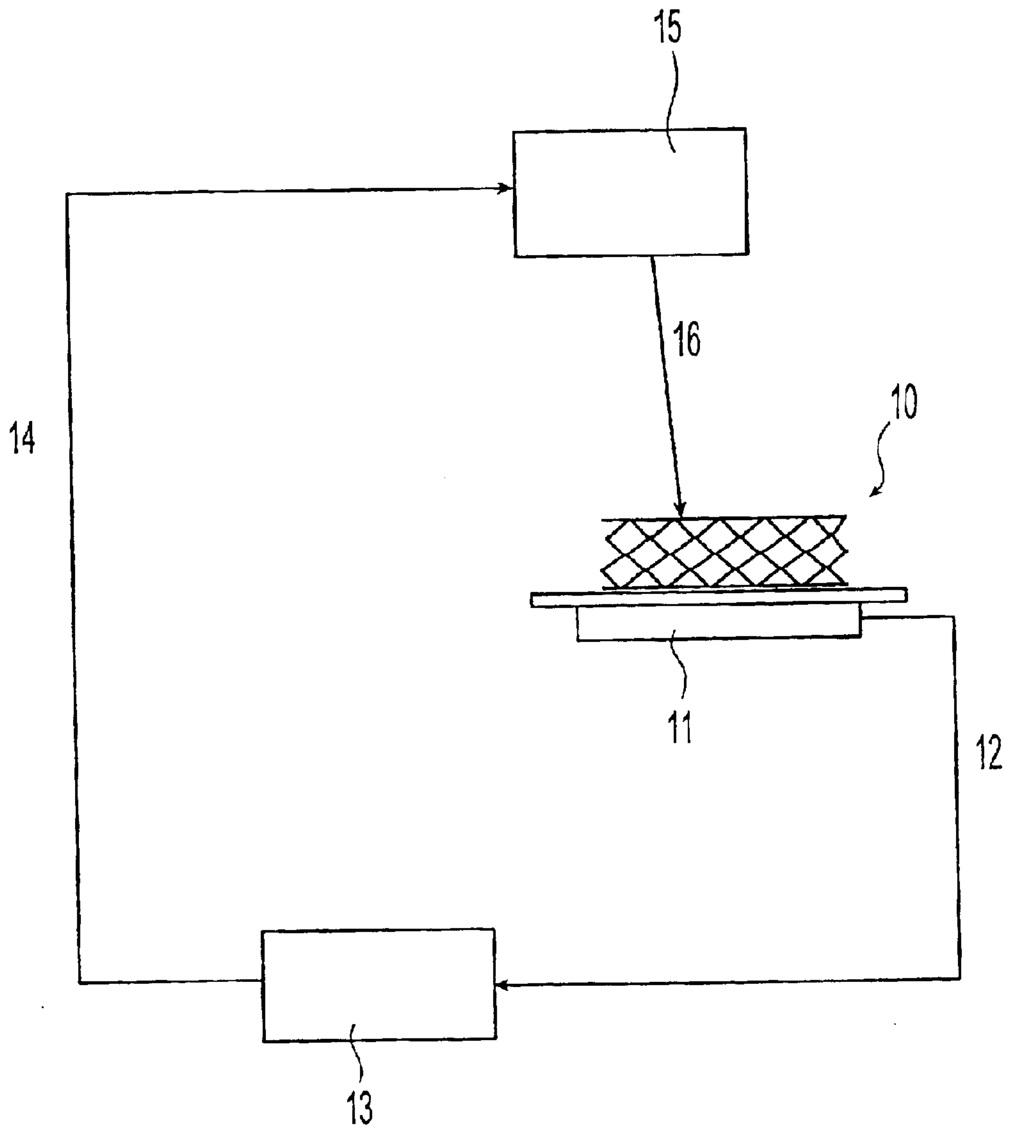
FIG. 1 shows a schematic diagram of an embodiment of the present invention in which a scale, an ultraviolet (UV) laser and a computer is used to make a coated medical device having a particular desired amount of coating.

The present invention is directed to a method for manufacturing an implantable medical device having a surface covered with a coating, using an ultraviolet (UV) laser.

1. Suitable Medical Devices

The method of the present invention is a method for manufacturing an implantable medical device having a surface adapted for exposure to body tissue of a patient. The medical devices suitable for the present invention include medical devices having at least a portion of a curved surface, which include, but are not limited to, stents, catheters, such as central venous catheters and arterial catheters, guidewires, cannulas, cardiac pacemaker leads or lead tips, cardiac defibrillator leads or lead tips, implantable vascular access ports, blood storage bags, blood tubing, vascular or other grafts, intra-aortic balloon pumps, heart valves, cardiovascular sutures, total artificial hearts and ventricular assist pumps, and extra-corporeal devices such as blood oxygenators, blood filters, hemodialysis units, hemoperfusion units or plasmapheresis units.

Medical devices which are particularly suitable for the present invention include stents, for example, vascular stents such as self-expanding stents and balloon expandable stents. Stents suitable for the present invention include any stent for medical purposes, which are known to the skilled artisan. Examples of self-expanding stents useful in the present invention are illustrated in U.S. Pat. Nos. 4,655,771 and 4,954,126 issued to Wallsten and 5,061,275 issued to Wallsten et al. Examples of appropriate balloon-expandable stents are shown in U.S. Pat. No. 5,449,373 issued to Pinchasik et al. Similarly, urinary implants such as drainage catheters are also appropriate for the invention. Stents having a complicated geometry pattern are particularly suitable for the method of the present invention. Examples of suitable stents include a stent having a surface which has a plurality of openings therein and a stent having a surface comprising a plurality of struts.

Appropriate materials for making the medical device of the present invention includes metals and polymers. Examples of such polymers include poly(ethylene terephthalate), polyacetal, poly(lactic acid), poly(ethylene oxide)/poly(butylene terephthalate) copolymer, and polycarbonate. Examples of suitable metals include titanium, stainless steel, platinum, tantalum or gold/platinum alloy.

2. Coating Compositions

In the present invention, any method for applying a coating composition to a surface of a medical device to form a coating is suitable. Examples of suitable methods include dipping, spraying, covering, plating, co-extruding and immobilizing. More than one coating method can be used to make a medical device. In the method of the present invention, any method for applying a coating composition known in the art is suitably used regardless of whether the method gives better control over the amount of coating on a medical device and whether the method provides less webbings in openings of a surface of a medical device. For example, a dip coating method can be used although the method gives less control over the amount of coating applied to a medical device than a spray coating method and tends to cause webbing in the openings of a surface of a medical device. A portion of the coating applied by dipping on a surface of a medical device can be ablated using an ultraviolet (UV) laser in the method of the present invention as described below in detail.

In the present invention, the term "applying in substantially the same manner," when referring to the application of a coating composition, means applying the coating composition in a manner wherein substantially all the parameters which affect the thickness of the coating formed are substantially identical. Such parameters include ambient temperature, humidity, air pressure, temperature of the coating composition, concentration of the composition, and all physical properties of the coating composition, e.g., viscosity and adhesiveness. When the coating composition is applied by a spray coating method, the factors further include spraying time and speed of the coating composition at the nozzle of the spraying apparatus as well as the type of nozzle employed, size of droplets and distance between the medical device and the nozzle. When a dipping method is used, the factors further include dipping time and speed of withdrawal of the medical device from the coating composition. Preferably, when two or more medical devices are coated in substantially same manner, they may be coated simultaneously. When two or more medical devices that are made of the same material and have substantially the same configuration and same dimensions, are coated in a substantially same manner, the thickness of the coating on each device can be presumed to be identical, and the thickness of the coating of one device is estimated by measuring thickness of the coating on the other device as explained in detail in section 5, infra.

Furthermore, before applying the coating composition, the surface of the medical device is optionally subjected to a pre-treatment, such as roughing, oxidizing or priming. Exposing the surface of the device to a primer is a preferable as method of pretreatment.

The thickness of the coatings formed by the method of the invention can range from almost a single layer of molecules to about 0.1 mm. Suitable thicknesses for the coating are known in the art and can be selected by the skilled artisans.

Coating compositions suitable for the present invention include a coating material dispersed or dissolved in a solvent suitable for the medical device which is known to the skilled artisan. Suitable coating materials include polymeric material, such as poly-L-lactic acid, polycarbonate, polyethylene terephtalate, silicones, polyurethanes, thermoplastic elastomers, ethylene vinyl acetate copolymers, polyolefin elastomers, hydrogels, ethylene-propylene-diene (EPDM) rubbers and styrene-isobutylene-styrene (SIBS).

Also, the coating can be a drug-releasing coating which immediately or gradually releases a biologically active material. Coating polymers useful for drug coatings includes hydrogel polymers which are often used to contain the biologically active material and are disclosed in U.S. Pat. No. 5,304,121, U.S. Pat. No. 5,464,650, PCT publication WO95/03083 and U.S. Pat. No. 5,120,322, which are incorporated herein by reference. However, a non-hydrogel can be also used. Such coatings include biologically active molecules, such as heparine or insuline molecules, directly attached to oxide molecules on the surface of the structure as explained below. Although polymeric molecules can be combined with biologically active molecules, biologically active materials can be directly immobilized on the polymeric molecules on the surface of the medical device. As disclosed in U.S. Pat. No. 5,356,433 to Rowland et al., polysaccharides can be immobilized to metallic surfaces by applying an organosilane coating with amine functionality and then applying a polysaccharide using carbodiimide as a coupling agent. U.S. Pat. No. 5,336,518 to Narayanan et al. also discloses that a polysaccharide can be immobilized on a surface by applying a coat of heptafluorobutylmethacrylate (HFBMA) by radio-repetition rate (RF) plasma deposition, creating functional groups on the surface by RF plasma with water vapor, and then applying the polysaccharide using carbodiimide. Moreover, examples of medical devices, in particular, stents coated with polymer/biologically active material coatings are described in U.S. Pat. No. 5,879,697 which is incorporated herein by reference.

The term "biologically active material" encompasses therapeutic agents, such as drugs, and also genetic materials and biological materials. The genetic materials mean DNA or RNA, including, without limitation, of DNA/RNA encoding a useful protein stated below, intended to be inserted into a human body including viral vectors and non-viral vectors. Viral vectors include adenoviruses, gutted adenoviruses, adeno-associated virus, retroviruses, alpha virus (Semliki Forest, Sindbis, etc.), lentiviruses, herpes simplex virus, ex vivo modified cells (e.g., stem cells, fibroblasts, myoblasts, satellite cells, pericytes, cardiomyocytes, sketetal myocytes, macrophage), replication competent viruses (e.g., ONYX-015), and hybrid vectors. Non-viral vectors include artificial chromosomes and mini-chromosomes, plasmid DNA vectors (e.g., pCOR), cationic polymers (e.g., polyethyleneimine, polyethyleneimine (PEI)) graft copolymers (e.g., polyether-PEI and polyethylene oxide-PEI), neutral polymers PVP, SP1017 (SUPRATEK), lipids or lipoplexes, nanoparticles and microparticles with and without targeting sequences such as the protein transduction domain (PTD). The biological materials include cells, yeasts, bacteria, proteins, peptides, cytokines and hormones. Examples for peptides and proteins include growth factors (FGF, FGF-1, FGF-2, VEGF, Endotherial Mitogenic Growth Factors, and epidermal growth factors, transforming growth factor $\alpha$ and $\beta$, platelet derived endothelial growth factor, platelet derived growth factor, tumor necrosis factor $\alpha$, hepatocyte growth factor and insulin like growth factor), transcription factors, proteinkinases, CD inhibitors, thymidine kinase, and bone morphogenic proteins (BMP's), such as BMP-2, BMP-3, BMP-4, BMP-5, BMP-6 (Vgr-1), BMP-7 (OP-1), BMP-8. BMP-9, BMP-10, BMP-11, BMP-12, BMP-13, BMP-14, BMP-15, and BMP-16. Currently preferred BMP's are BMP-2, BMP-3, BMP-4, BMP-5, BMP-6, BMP-7. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells include whole bone marrow, bone marrow derived mono-nuclear cells, progenitor cells (e.g., endothelial progentitor cells) stem cells (e.g., mesenchymal, hematopoietic, neuronal), pluripotent stem cells, fibroblasts, macrophage, and satellite cells.

Biologically active material also includes non-genetic therapeutic agents, such as:

- anti-thrombogenic agents such as heparin, heparin derivatives, urokinase, and P-Pack (dextrophenylalanine proline arginine chloromethylketone);
- anti-proliferative agents such as enoxaprin, angiopeptin, or monoclonal antibodies capable of blocking smooth muscle cell proliferation, hirudin, and acetylsalicylic acid, amlodipine and doxazosin;

anti-inflammatory agents such as glucocorticoids, betamethasone, dexamethasone, prednisolone, corticosterone, budesonide, estrogen, sulfasalazine, and mesalamine;

antineoplastic/antiproliferative/anti-miotic agents such as paclitaxel, 5-fluorouracil, cisplatin, vinblastine, vincristine, epothilones, methotrexate, azathioprine, adriamycin and mutamycin; endostatin, angiostatin and thymidine kinase inhibitors, taxol and its analogs or derivatives;

anesthetic agents such as lidocaine, bupivacaine, and ropivacaine;

anti-coagulants such as D-Phe-Pro-Arg chloromethyl keton, an RGD peptide-containing compound, heparin, antithrombin compounds, platelet receptor antagonists, anti-thrombin anticodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors and tick antiplatelet peptides;

vascular cell growth promotors such as growth factors, Vascular Endothelial Growth Factors (FEGF, all types including VEGF-2), growth factor receptors, transcriptional activators, and translational promotors;

vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;

cholesterol-lowering agents; vasodilating agents; and agents which interfere with endogenous vasoactive mechanisms;

anti-oxidants, such as probucol;

antibiotic agents, such as penicillin, cefoxitin, oxacillin, tobranycin angiogenic substances, such as acidic and basic fibrobrast growth factors, estrogen including estradiol (E2), estriol (E3) and 17-Beta Estradiol; and drugs for heart failure, such as digoxin, beta-blockers, angiotensin-converting enzyme (ACE) inhibitors including captopril and enalopril.

A coating of a medical device of the present invention may contain multiple coating layers. For example, the first layer and the second layer may contain different biologically active materials. Alternatively, the first layer and the second layer may contain an identical biologically active material having different concentrations. Either of the first layer or the second layer may be free of biologically active material.

3. Suitable Ultraviolet Lasers

In embodiments of the present invention, after a surface of a medical device is coated, a portion of the coating may be ablated using an ultraviolet (UV) laser (light amplification by stimulated emission of radiation). In the present invention, an “UV” or “ultraviolet” laser means a laser having wavelength less than about 400 nm. Preferably, the wavelength of the ultraviolet (UV) laser used in the method of the present invention is shorter than about 200 nm. Because of the relatively shorter wave length, the ultraviolet (UV) laser ablates a coating material by a photochemical reaction rather than a thermal reaction. Because the ablation is accompanied by substantially no heat transfer or a thermal shock, it does not cause serious damages, such as cracking to the coating material. Also, the ablated surface is substantially free from redeposited or re-solidified material. For the same reason stated above, such ultraviolet (UV) laser should have a pulse length shorter than about 100 nano ($10^{-9}$) seconds and a repetition rate less than about 100 Hertz (Hz). Preferable examples of the ultraviolet (UV) laser useful for the present invention include a neodymium YAG (Nd:YAG) (355 nm) laser, a triple harmonic frequency (THF) laser, an argon fluoride (ArF) laser having 193 nm wavelength and a fluorine ($F_2$) laser having 152 nm wavelength. In particular, excimer lasers which are commercially available from Lamda Physik, Inc., can be used for a method of the present invention.

In one preferable embodiment of the present invention, ultraviolet (UV) laser ablation may be conducted with an ultrashort-pulse laser. “Ultrashort-pulse lasers” refer to lasers consisting of pulses with durations shorter than about 10 pico ($=10^{-11}$) second. The ultrashort-pulse lasers are known to artisans. For example, they are thoroughly disclosed by M. D. Perry et al. in *Ultrashort-Pulse Laser Machining*, Section K-ICALEO 1998, pp. 1–20, which is incorporated herein by reference. In the method of the present invention, because of use a laser having rather short pulse length, the laser ablation is very accurately controlled and creates substantially no heat.

The intensity (fluence) of the laser radiation that is required to trim a material is dependent on the material to be ablated. By adjusting the intensity of the ultraviolet (UV) laser, it is possible to ablate the entire thickness of the coating material and not to ablate the substrate or the medical device. Alternatively, the thickness of the coating is estimated before ablation, the intensity and/or pulse number of the ultraviolet (UV) laser can be adjusted to properly ablate the estimated thickness. Specifically each material has its own laser-induced optical breakdown (LIOB) threshold which characterizes the fluence required to ablate the material at a particular pulse width. Also the fluence of the laser suitable for the present invention can be chosen according to the thickness of the coating. Furthermore, the number of pulses needed to ablate completely through a material can be calculated for a given energy or fluence. It is possible to choose an ultraviolet (UV) laser having an appropriate intensity so that the ultraviolet (UV) laser can trim the coating but cannot ablate the stent body. For example, an ultraviolet (UV) laser can be adjusted to trim a coating material but does not ablate a metallic stent body. One of ordinary skill can choose the suitable intensity for ablating the coating material.

In certain embodiments of the present invention, the coating on the medical device has more than one layer. Using an ultraviolet (UV) laser adjusted to ablate only the top layer, it is possible to ablate a portion of the top layer substantially without damaging the other layer(s). Such ultraviolet (UV) laser can be adjusted based on the thickness of the top layer that is estimated as explained in section 5, infra. For example, it is possible to remove a portion of the top layer from a middle section of the coated medical device, such as a stent, and leave the top layer at the both end sections of the coated device. For example, if the top layer contains the same kind of the biologically active material than that of the layer below at a higher concentration, then a medical device having a higher concentration of the biologically active material at its two end sections than its middle section can be obtained. Alternatively, the portion of the top layer that is removed from a portion of the top layer can have various shapes, such as a spiral shape, a strip-like shape, or a ring shape.

Furthermore, the portion of the top layer can contain a biologically active material that is different from the one contained in the under layer. Accordingly, a medical device which can release two different biologically active materials is obtained. Alternatively, the top layer can be substantially free of a biologically active material and the under or inner layer can contain a biologically active material. By ablating a portion of a top layer, a coated medical device wherein the coating containing a biologically active material covered with a discontinuous top layer free of biologically active material can be achieved.

4. Manufacturing a Coated Medical Device Having a Desired Amount of Biologically Active Material In one embodiment of a method of the present invention, a coated medical device in which the coating contains a desired amount of a biologically active material is prepared. In this embodiment, the amount of biologically active material in a coating placed on a medical device is determined by a method known by one or ordinary skill in the art. For example, a medical device, such as a stent or portion thereof, which is to be coated is weighed. Then, a coating composition containing a biologically active material is applied to a surface of the device in a manner such that a coating containing an amount of biologically active material in excess of the desired amount of biologically active material is formed. The coated device is weighed to determine the excess amount of biologically active material in the coating. Specifically, by weighing the coated device, the amount of coating placed on the device can be determined. Based on this amount of coating and concentration of the biologically active material in the coating composition, the skilled artisan can determine the amount of coating that contains the excess amount of the biologically active material. Afterwards, a portion of the coating is ablated with an ultraviolet (UV) laser to obtain a coated medical device wherein the coating contains a desired amount of biologically active material. The desired amount of biologically active material may be a range having a minimum desired amount and a maximum desired amount.

In the present invention, the term “weighing” encompasses all ways of weighing. For example, a medical device can be hung or be placed on a plate for weighing. In one preferred embodiment, the device for weighing is connected to a fixture to which the medical device is attached during the laser ablation. The fixture is connected to a scale so that the medical device can be continuously weighed. Preferably, the weighing device is connected to a computer which can record, compare and calculate the weight data received from the weighing device.

In a preferred embodiment, the ultraviolet (UV) laser ablation is controlled by a computer which receives the weight data from the weighing device. FIG. 1 is a schematic diagram which shows how a scale, a laser and a computer relate to each other for conducting this embodiment of the invention. A stent 10 is weighed by a scale 11. The weight measured by the scale 11 is recorded by a computer 13. The flow of the data is shown by an arrow 12. After a coating composition is applied to the surface of the stent, the stent 10 is weighed again by using the scale 11. Based on the weight data received from the scale 11, the computer 12 determines the excess amount of the coating and commands an ultraviolet (UV) laser 15 to ablate a portion of the coating to remove the excess. The flow of the command is shown by an arrow 14. The desired portion of the coating on the stent 10 is ablated by the ultraviolet (UV) laser 15, and such action is shown by an arrow 16.

In one embodiment, the coated device may be weighed again after ablation to determine if there is still an excess amount of biologically active material or coating on the device. In this embodiment, these ablation and weighing steps are repeated until a coated device having the desired amount of biologically active material in the coating is obtained.

In another embodiment, the thickness of the coating may be estimated before the ablation. In yet another embodiment, the size of the portion of the coating that is ablated is determined before the portion is ablated. Such size may be determined based on the weight of the coating to be ablated and an estimated thickness of the coating. The thickness of the coating is estimated by a method explained in section 5, infra.

Furthermore, a coating of a medical device of the present invention may consist of a plurality of coating layers. In one embodiment of the present invention, a medical device covered by the coating having the outermost layer containing a desired amount of biologically active material can be prepared. In this embodiment, only the outermost coating layer is ablated without ablating the under layer(s). The thickness of the outermost layer may be estimated before the ablation, and the ultraviolet (UV) laser may be adjusted to ablate the outermost layer but not the other layer(s).

5. Estimation of Thickness of Coating

In one embodiment of the present invention, the thickness of a coating on a medical device can be measured. In such embodiment, a portion of a coating on a medical device is ablated with an ultraviolet (UV) laser to expose a portion of the surface of the medical device and create a step in the coating. By adjusting the intensity of the ultraviolet (UV) laser, it is possible to ablate the entire thickness of the coating material and not to ablate the medical device. Alternatively, especially when the medical device is made of a polymer, the coated medical device is slowly ablated, and the chemical composition of the ablated material is continuously detected using an instrument, such as a mass spectrometer during the ablation. The laser ablation is continued until the chemical composition of the material that makes up the medical device is detected, indicating that the entire thickness of the coating has been ablated through.

Figure 5:
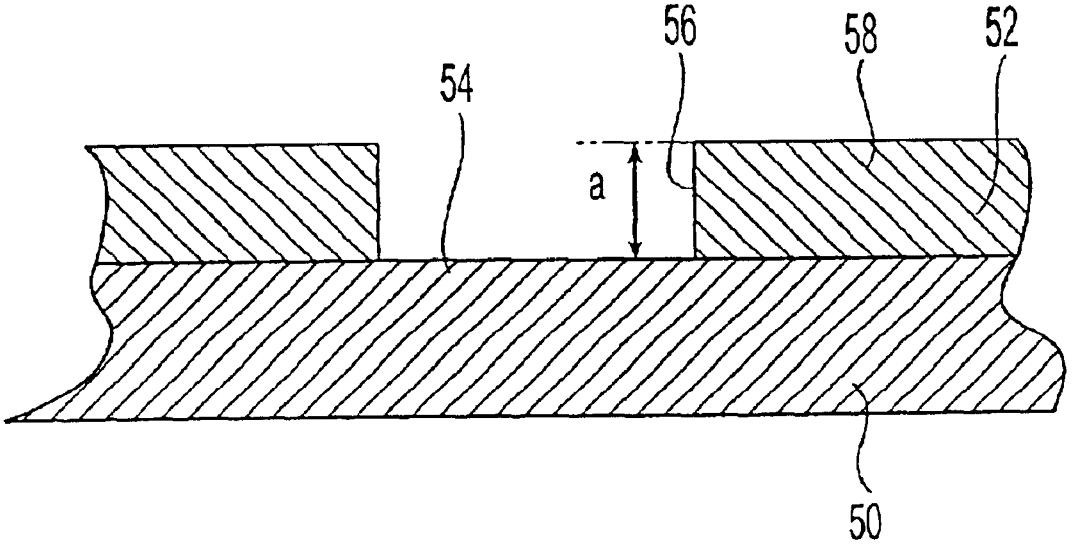
FIG. 5 is a cross-sectional view of a coated medical device wherein a portion of the coating is ablated to expose a portion of the surface of the device.

The term “step” in the present invention means a structure similar to a step of a stairway as shown in FIG. 5. In FIG. 5, a portion of a coating 52 is ablated to expose a portion of surface of the medical device 50. A step comprises a portion of the medical device’s surface 54, the cross-section 56 of the coating 52 and a portion of the coating’s surface 58. The thickness a of the coating can be determined by measuring the height of the step.

The step height, i.e., a thickness of the coating, can be optically measured by using a white light interferometer. White light is defined as polychromatic light which contains lights of various wavelength. An interferometer is an optical instrument for measuring the thickness of a layer. The “Michelson interferometer” is a well-known example of an interferometer. A white light interferometer is commercially available, for example from Zygo Corporation. In a preferred embodiment of the present invention, the white light interferometer is connected to a computer wherein the data obtained by the white light interferometer is processed. Preferably, the computer also receives the weight data and controls the ultraviolet (UV) laser ablation of the coating. NEWVIEW™ 5000 sold from Zygo Co. and WYKO NT3300™ from VEECO Instruments are examples for such systems that are commercially available.

In embodiments of the present invention, a thickness of a coating of a coated medical device is estimated before the coating is ablated. Specifically, a second medical device, which is made of the same material as a first medical device that is to be coated and having substantially the same configuration and dimensions as the first medical, is weighed. Then, a coating composition is applied to a surface of the second device in a substantially same manner as the coating composition that was applied to a surface of the first medical device. The measured thickness of the coating on the second medical device is used as an estimated thickness of the coating on the first medical device. In one embodiment, two or more portions of the coating on the second medical device are ablated using an ultraviolet (UV), and the thicknesses at each portion of coating are determined. An average is taken of these thicknesses. The average thickness of the coating on the second medical device is used as an estimated thickness of the coating on the first medical device. In yet another embodiment, at least one additional medical device is used in conjunction with the second medical device to estimate the coating thickness. After determining the thickness of the coating on each medical device, an average of the thicknesses is used as the estimated thickness of the coating on the first medical device.

Moreover in another embodiment of the present invention, a coating comprises a plurality of layers. The thickness of the second layer is estimated by measuring the thickness of coating layer(s) before and after the second layer is applied. Specifically, to estimate the thickness of the second layer of a first coated medical device wherein the coating has the second layer and a first layer, a second medical device and a third medical device are used. After applying a first coating composition to the surfaces of each medical device to be coated in substantially same manner to form a first layer of the coating, the thickness of the first layer of the second medical device is measured as explained above. Afterward, a second coating composition is applied to the first and third medical devices in substantially the same manner to form the second layer of the coating. The total thickness of the second layer and the first layer of the third medical device is measured as explained above, i.e., by creating a step in the entire coating and measuring thickness thereof. By subtracting the thickness obtained for the first layer of the second medical device from the total thickness of the coating obtained for the third medical device. The thickness of the second layer in the coating on the third medical device is obtained. The thickness of the second layer of the first medical device is estimated as the thickness of the second layer of the third medical device. In a similar manner, the thickness of a layer in a coating having three or more layers can also be estimated by using more medical devices.

In another embodiment, more than one portion of the coating on the second medical device and/or the third medical device are ablated using an ultraviolet (UV), and the thickness of the coating at each portion is determined and averaged. The average of the measured thicknesses is used to estimate the thickness of the second layer of the first medical device. In yet another embodiment, at least one additional medical device is used in conjunction with the second and/or third medical device. For instance, the additional medical device can be coated only with the first layer like the third medical device. After determining the thicknesses of the first layer on the third and the additional medical device(s), an average of the thicknesses is used to estimate the thickness of the second layer on the first medical device.

6. Coated Medical Devices with a Portion of Their Coatings Removed

Figure 2:
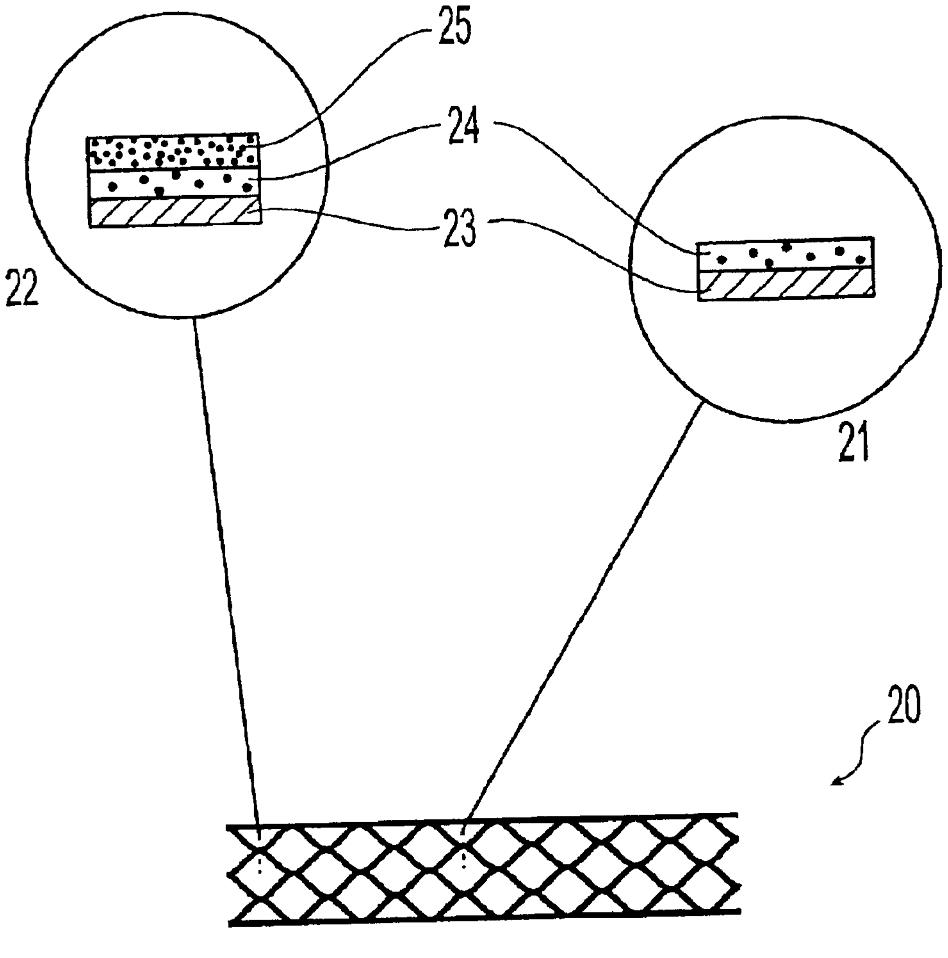
FIG. 2 shows a schematic view of a stent having a single-layered coating on its middle section and having a two-layered coating at an end of the stent.

In other embodiments of the invention, a portion of coating on a coated medical device is ablated by an ultraviolet (UV) laser. In one embodiment, after estimating the thickness of a top layer of the coating of a medical device coated with an under layer and a top layer (see section 5, supra), the top layer is ablated only at the middle portion of the coated device. An ultraviolet (UV) laser adjusted based on the estimated thickness of the top layer is used to ablate or remove this portion of the top layer. In another embodiment, the top layer is slowly ablated or removed without estimation of thickness using ultraviolet (UV) laser while the chemical composition of the ablated material is continuously detected using an instrument, such as a mass spectrometer. The laser ablation is continued until the chemical composition of the under layer is detected. The coated device obtained after the above-mentioned laser ablation has at least two layers of coating at both ends of the device but one fewer layer at the middle of the device. An example of such a device is shown in FIG. 2. A stent 20 comprising struts 23 is coated with an under layer 24 containing a biologically active material on entire surface of the stent 20. Because the top layer of the coating near the middle of the stent has been ablated, there is no top layer of coating at the middle of the stent. However, at the ends of the stent, there is a top coating layer 25 of coating containing a higher concentration of the biologically active material. Each portion of the ends and of the middle portion of the stent is shown in a magnified cross-sectional view 21 and 22, respectively.

Figure 3:
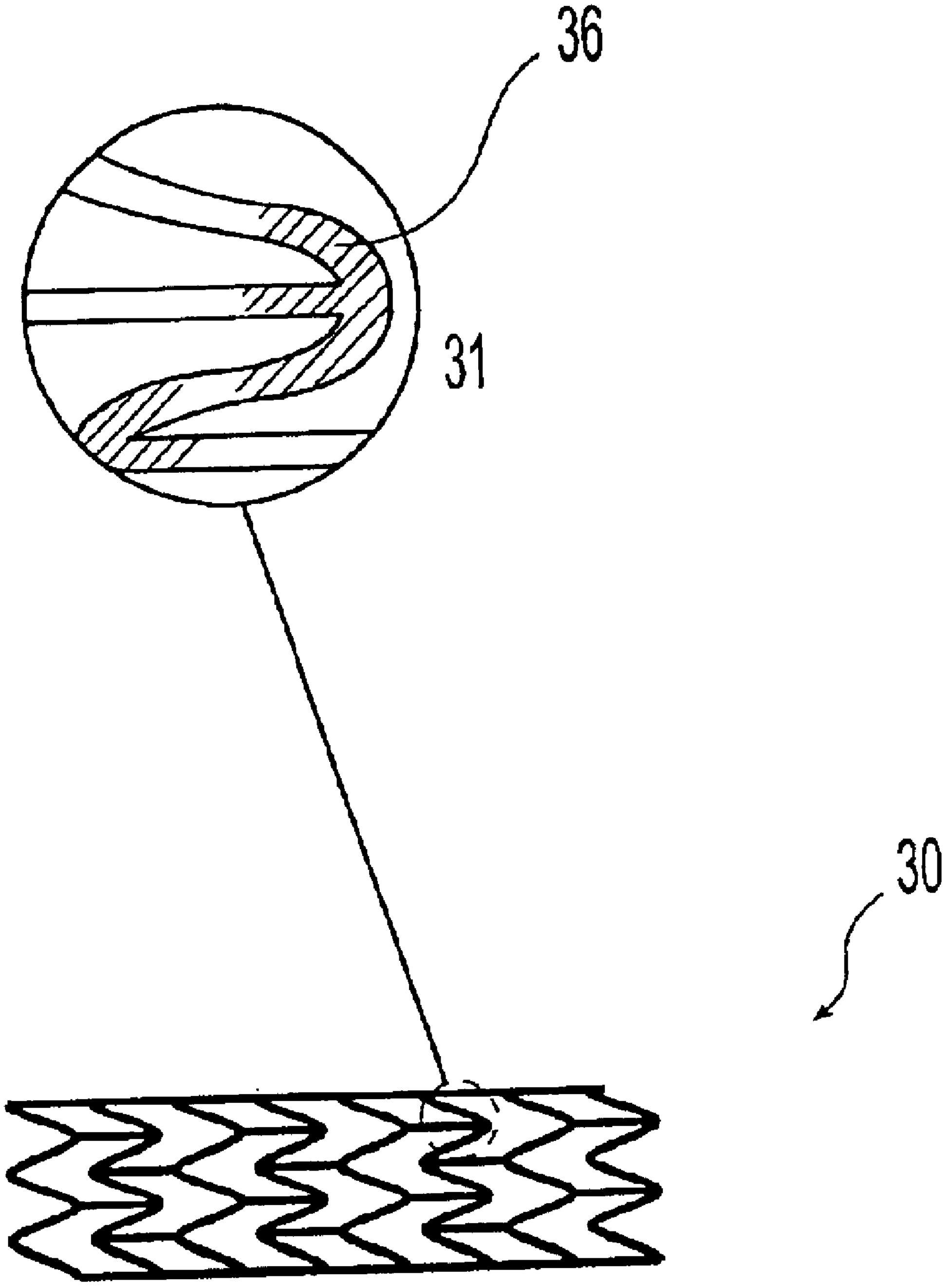
FIG. 3 shows a schematic view of a stent having a partially coated surface, that is prepared by an embodiment of the invention.

Furthermore, depend on its geometry, a medical device, such as a stent may have a portion where a thick coating placed on its surface may easily crack and cause problems. For example, when an expandable stent has a plurality of struts which are in close proximity to each other, the coating on the struts may adhere to each other when the stent is collapsed to be loaded into a delivery sheath. When the stent is deployed, the adhered coating may be torn off the stent. Also, in an expandable stent, there are portions in struts which are subjected to significant expansion forces, e.g., the portions 32 in FIG. 3. A coating on such portions has a great risk of cracking when the stent expands. In one embodiment of the present invention, portions of coating on an individual strut can be ablated with the ultraviolet (UV) laser to reduce such cracking or tearing. In FIG. 3, an expandable stent 30 is schematically shown. A portion of the stent 30 is magnified in circle 31 wherein shaded portions 32 indicate those portions of the coating in the strut that tend to crack or tear. The coating on the portion 32 is ablated with an ultraviolet (UV) laser ablation to prevent the cracking or tearing. In another embodiment, the coating at such portions 32 is not entirely ablated but may be thinned or made thinner leaving some coating to cover the device at those portions. Such ablation may be conducted using a ultraviolet laser which is adjusted to ablate only the coating material but not the medical device material or using a ultraviolet laser which is adjusted to ablate the thickness of the coating estimated beforehand.

7. Removing Webbing

When a medical device, such as a stent, has a sidewall made of struts that form openings therein, application of a coating composition may form not only a coating on the surface of the struts but also undesired webbing in the openings. A "webbing" is an excess coating material which bridges at small gaps or corners between stent struts and entirely or partially blocks the openings. Webbing is undesirable because it can separate from the device while it is implanted in a patient. Such separated or loose webbing can cause emboli. Dip coating tends to create an undesired amount of webbing of coating material. Such webbing can be ablated with the ultraviolet (UV) laser described above. Preferably, the ultraviolet (UV) laser is adjusted to ablate only the coating but not the medical device.

In a preferred embodiment, the ultraviolet (UV) laser ablation to remove the webbing is computer-controlled. Also, when the medical device used for the method of the present invention has an expandable portion, such ultraviolet (UV) laser ablation may be conducted while the device is in its expanded state.

EXAMPLE

Figure 4:
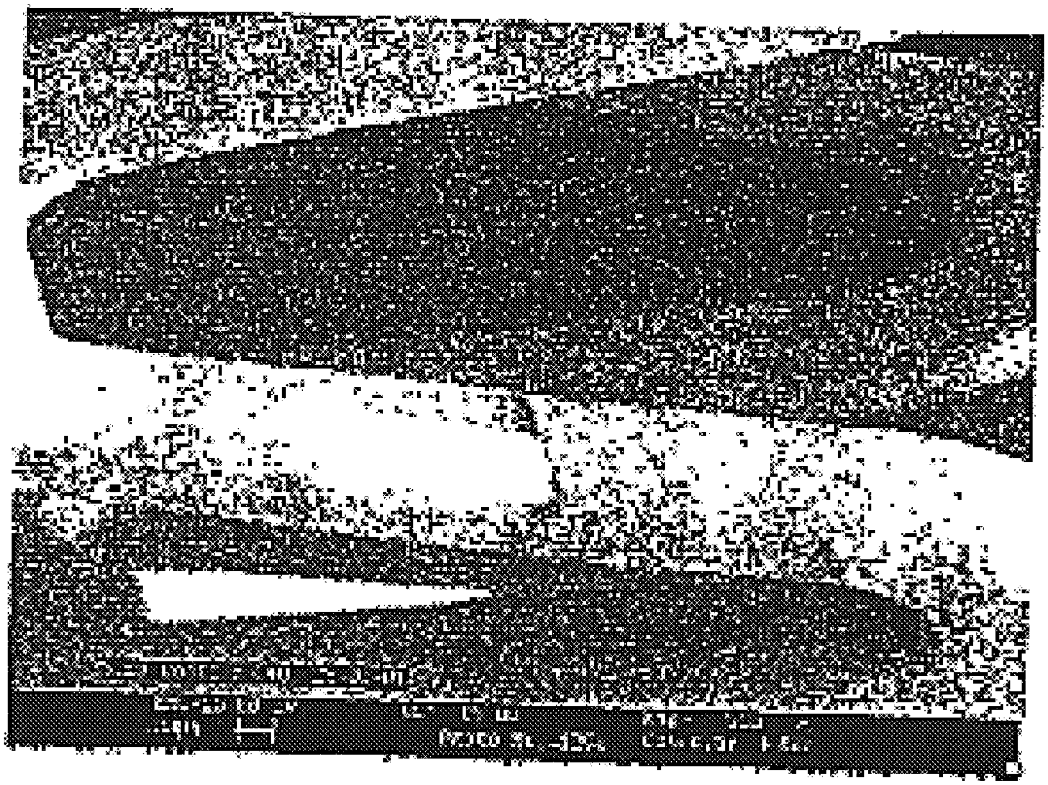
FIG. 4 is a micrograph (at magnification×500) of a coated stent wherein a portion of the coating has been ablated.

A stent made of stainless steel 316LVM was coated with a coating composition [coating polymer: styrene isobutylene styrene (SIBS), solvent: tetrahydrofuran (THF)]. A portion of the coating was ablated with an ultraviolet (UV) laser without ablating the stent body. The ultraviolet laser has the following properties: wavelength 193 nm, repetition rate 50 Hertz, number of pulses from 95 to 100, pulse duration 10 nano seconds and laser fluence $0.15/cm^2$. A micrograph at magnification×500 of the portion of the stent is shown as FIG. 4. The rectangular portion in white shown in the middle of FIG. 4 is an exposed metal surface from which the coating is removed by the ultraviolet (UV) laser ablation. The step height system of the coating was measured with a white light interferometer by using a NEWVIEW™ (Zygo Co.) system. The step height, i.e., the coating thickness was determined to be 19 $\mu$m.

The description contained herein is for purposes of illustration and not for purposes of limitation. Changes and modifications may be made to the embodiments of the description and still be within the scope of the invention. Furthermore, obvious changes, modifications or variations will occur to those skilled in the art. Also, all references cited above are incorporated herein, in their entirety, for all purposes related to this disclosure.

What is claimed is:

1. A method for manufacturing an implantable medical device having a surface adapted for exposure to body tissue of a patient, wherein at least a portion of the surface is covered with a coating having a desired amount of a biologically active material, said method comprising:

(a) providing a first medical device having a surface;

(b) applying to a portion of the surface of the first medical device a coating composition comprising the biologically active material in a manner such that a coating containing an amount of the biologically active material in excess of the desired amount of biologically active material is formed on the surface of the first medical device;

(c) estimating the thickness of the coating by:

(i) applying to at least a portion of a surface of a second implantable medical device the coating composition, in substantially the same amount and same manner that was used to form the coating on the surface of the first medical device, to form a coating on the surface of the second medical device, wherein the first and second medical devices are made of the same material and have substantially the same configurations and dimensions;

(ii) ablating a portion of the coating of the second medical device with the ultraviolet (UV) laser to expose a portion of the surface of the second medical device and to create a step having a height in the coating;

(iii) determining the thickness of the coating of the second medical device by measuring the height of the step using a white light interferometer; and (iv) estimating the measured thickness of the coating of the first medical device based on the thickness of the coating of the second medical device; and (d) ablating a portion of the coating of the first medical device containing the amount of biologically active material in excess of the desired amount using an ultraviolet (UV) laser.

2. The method of claim 1 which further comprises repeating steps (ii) and (iii) using a different portion of the coating of the second medical device and wherein an average of the measured thickness of the coating of the second medical device is obtained and wherein the thickness of the coating of the first medical device is estimated based upon the average.

3. The method of claim 1 which further comprises conducting steps (i), (ii) and (iii) using at least one additional implantable medical device; and wherein an average of the measured thickness of the coating of the second medical device and the measured thicknesses of the coating of the additional medical device(s) is obtained; and wherein the thickness of the coating of the first medical device is estimated based upon the average.

4. The method of claim 1, wherein the ultraviolet laser has pulse length shorter than about 100 nanoseconds and a repetition rate less than about 100 Hertz.

5. The method of claim 1 wherein the surface of the first medical device is curved.

6. The method of claim 1 wherein only the coating but not the first medical device is ablated.

7. The method of claim 1 wherein the coating comprises more than one layer, and the ablating step (d) is conducted on only the outermost layer of the coating.

8. The method of claim 1, wherein the steps (c) and (d) are repeated as necessary until the coating contains the desired amount of biologically active material.

9. The method of claim 1 wherein the laser has a wavelength between about 157 nm and about 193 nm.

10. The method of claim 1 wherein the coating composition comprises a polymeric material which is selected from the group consisting of poly-L-lactic acid, polycarbonate, polyethylene terephtalate, silicones, polyurethanes, thermoplastic elastomers, ethylene vinyl acetate copolymers, polyolefin elastomers, hydrogels and ethylene-propylene-diene (EPDM) rubbers.

* * * * *